US00PP34245P2

(12) United States Plant Patent
Ranney et al.

(10) Patent No.: US PP34,245 P2
(45) Date of Patent: May 17, 2022

(54) ***LIGUSTRUM OVALIFOLIUM* PLANT NAMED 'NCLO1'**

(50) Latin Name: *Ligustrum ovalifolium*
Varietal Denomination: NCLO1

(71) Applicant: North Carolina State University, Raleigh, NC (US)

(72) Inventors: Thomas Green Ranney, Arden, NC (US); Darren Touchell, Raleigh, NC (US); Irene Palmer, Raleigh, NC (US); Andra Nus, Raleigh, NC (US); Nathan P. Lynch, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 17/342,775

(22) Filed: Jun. 9, 2021

(51) Int. Cl.
*A01H 5/02* (2018.01)
*A01H 6/00* (2018.01)

(52) U.S. Cl.
USPC ..... Plt./226
CPC ..... *A01H 6/00* (2018.05)

(58) Field of Classification Search
USPC ..... Plt./226
CPC ..... A01H 5/02; A01H 5/00
See application file for complete search history.

*Primary Examiner* — Kent L Bell
(74) *Attorney, Agent, or Firm* — Cassandra Bright

(57) ABSTRACT

A new and distinct cultivar of *Lilgustrum* plant named 'NCLO1' with a compact habit and uniquely variegated, semi-evergreen foliage. 'NCL01' is a new cultivar of privet, suitable for landscape purposes.

3 Drawing Sheets

Latin name of the genus and species: *Ligustrum ovalifolium.*

Variety denomination: 'NCLO1'.

BACKGROUND OF THE INVENTION

The present invention comprises a new and distinct privet cultivar hereinafter referred to by the cultivar name 'NCLO1'. This new privet was developed through a breeding program at Mills River, N.C. 'NCLO1' was selected from a population of seedlings derived from an open-pollinated *Ligustrum ovalifolium* 'Vicaryi' (NCSU 2003-098, unpatented). The first asexual propagation of 'NCLO1' was carried out in July 2012 by rooting stem cuttings at Mills River, N.C. and has been asexually reproduced repeatedly by vegetative cuttings over a 9-year period. 'NCLO1' roots readily from softwood cuttings treated with a basal dip of 2,500-5,000 ppm indole butyric acid (potassium salt) in water. Stem cuttings initiate roots in approximately 4 to 6 weeks and a well-rooted plant can be produced within 12 to 14 weeks. 'NCLO1' has been found to retain its distinctive characteristics through successive asexual propagations.

SUMMARY OF THE INVENTION

The following are the unique characteristics of this new cultivar when grown under standard horticultural practices at Mills River, N.C.

1. Uniquely variegated cream to yellow-edged foliage.
2. Compact plant habit.
3. Semi-evergreen.

COMPARISON WITH PARENT VARIETIES

'NCLO1' is distinguished from *Ligustrum ovalifolium* 'Vicaryi' in that *Ligustrum ovalifolium* 'Vicaryi' has yellow foliage whereas 'NCLO1' has variegated cream to yellow-edged foliage as described below.

COMPARISON WITH COMMERCIAL CULTIVARS

'NCLO1' can be compared to the unpatented commercial variety 'Jack Frost', which also has variegated foliage. 'NCLO1' is distinguished from *Ligustrum japonicum* 'Jack Frost' in that 'NCLO1' is semi-evergreen, whereas 'Jack Frost' is fully evergreen. Plants of the new variety are smaller and more compact than plants of 'Jack Frost' and hold the variegated foliage pattern during Winter months. 'Jack Frost' loses foliar variegation during the Winter months.

BRIEF DESCRIPTION OF THE DRAWINGS

This new privet is illustrated by the accompanying photographs, which show the plant's form and foliage. The colors shown are as true as can be reasonably obtained by conventional photographic procedures. Colors in the photographs may differ slightly from the color values cited in the detailed botanical description, which accurately describe the colors of the new privet.

DETAILED BOTANICAL DESCRIPTION

Figure 1:
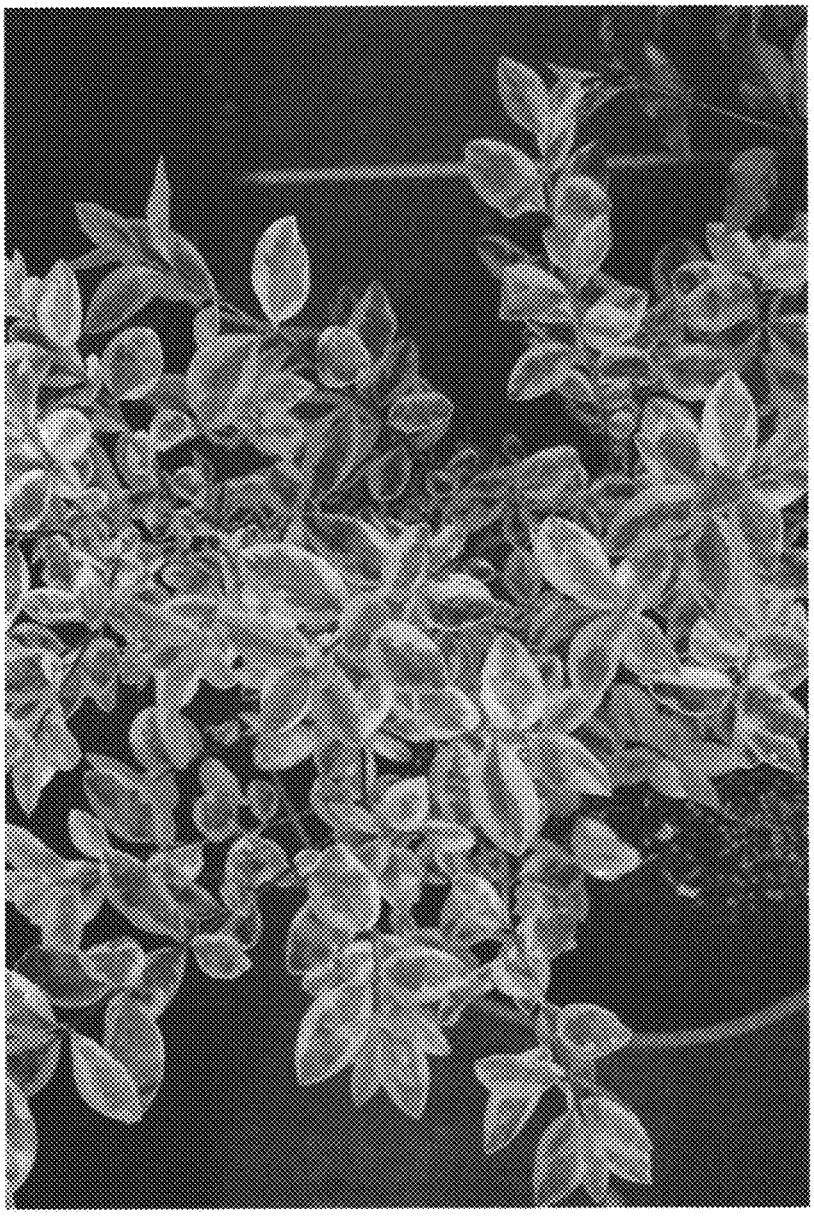
FIG. 1 is a photograph of the variegated foliage of 'NCLO1' taken in October, 2020 in Grand Haven, Mich. The plant in this photograph is approximately 18 months of age.
Figure 2:
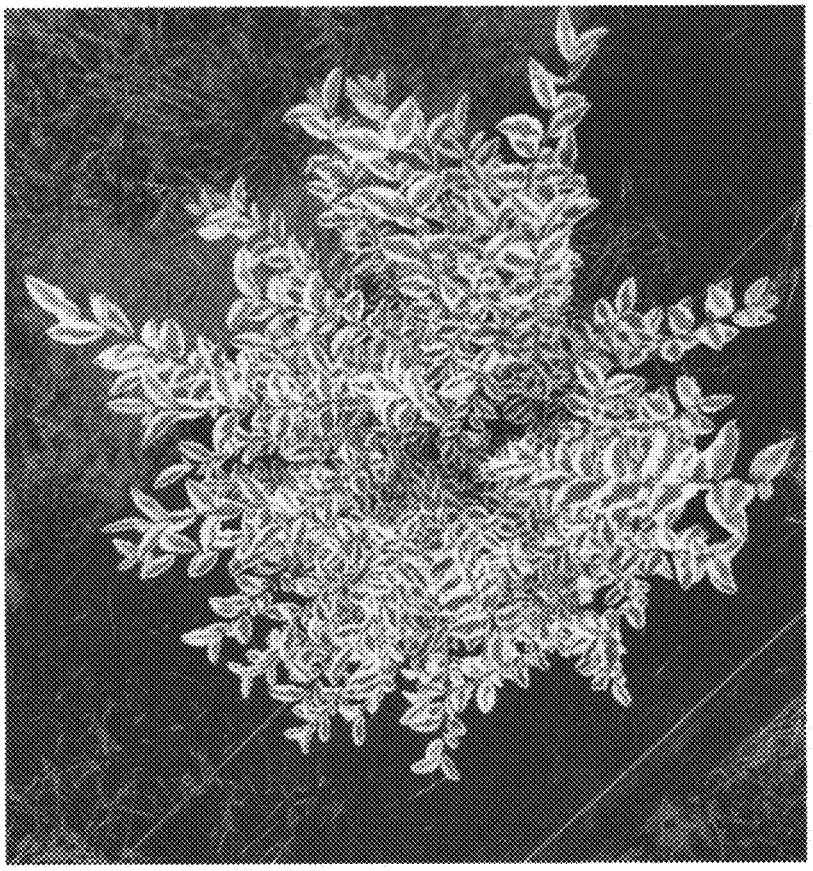
FIG. 2 is a photograph of a three-year-old, field-grown plant of 'NCLO1' taken in October, 2020 in Grand Haven, Mich.
Figure 3:
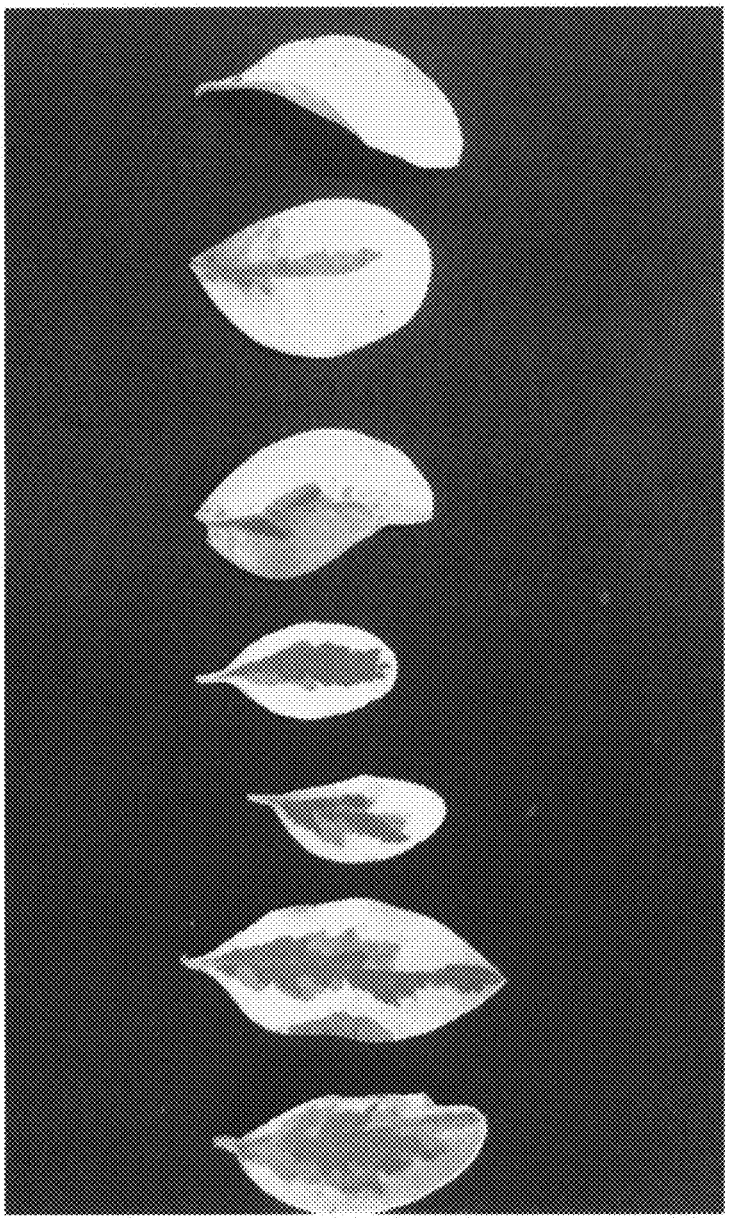
FIG. 3 is a photograph showing variation in color and variegation patterns of the foliage of 'NCLO1' taken in Mills River, N.C. in April 2021.

The following is a detailed description of the botanical characteristics of the new and distinct privet variety plant known by the denomination 'NCLO1'. The detailed description was taken on a three-year-old container-grown plant in Mills River, N.C. in 2020. All colors cited herein refer to The Royal Horticultural Society Colour Chart (The Royal Horticultural Society (R.H.S.), London, Sixth Edition). Where specific dimensions, sizes, colors, and other characteristics are given, it is to be understood that such characteristics are approximations or averages set forth as accurately as practicable.

Classification:

*Botanical name.*—*Ligustrum ovalifolium.*

*Common name.*—Privet.

*Parentage.*—Selected from a population of seedlings of derived from an open-pollinated *Ligustrum ovalifolium* 'Vicaryi' NCSU 2003-098 (unpatented). Although the maternal parent was previously classified as a hybrid between *Ligustrum ovalifolium* and *L. vulgare* and given the hybrid designation of *L.* × *vicaryi*, more recent research has concluded this taxon is a selection of *L. ovalifolium* with corrected nomenclature of *L. ovalifolium* 'Vicaryi' (Edwards et al., 2015).

PLANT

Growth habit: Compact.

Height: About 35 cm.

Width: About 35 cm.

Shoots and branches:

*Shoots* (*current year's growth*).—Color: Greyed-Green (199B). Texture: Glabrous.

*Shoots* (*prior year's growth*).—Color: Greyed-Green (199B). Texture: Glabrous.

*Branches* (*woody branches* 2-4 *years old*).—Branch length: Avg. 14 cm (range 3.3 to 28.8 cm). Branch diameter: Avg. 0.3 cm (0.1 to 0.9 cm). Color: Greyed-Green (199B). Texture: Glabrous.

Internode length: Avg. 1.8 cm (1.2 to 2.7 cm).

FOLIAGE

Type: Simple.

Persistence: Semi-evergreen.

Arrangement: Opposite.

Shape: Obovate.

Length of lamina: Avg. 2.0 cm (1.0 to 3.4 cm).

Width of lamina: Avg. 1.1 cm (0.7 to 2.1 cm).

Emerging leaves:

*Color.*—Irregular marginal variegation covers 50-90% of leaf area. Upper margin: Varies from Strong Yellowish Green (N144A) to Strong Yellow (N144B). Upper center: Varies from Green (141A) to Moderate Yellow Green (147C). Lower margin: Varies from Strong Yellowish Green (N144B) to Strong Yellow (N144C). Lower center: Varies from Green (141A) to Moderate Yellow Green (147C).

Mature leaves during growing season:

*Color.*—Irregular marginal variegation covers 50-90% of leaf area. Upper margin: Varies from Greyed-Yellow (162B) to Yellow (10A). Upper center: Irregular blotch with patches of Green (NN137A) and Greyed-Green (191A). Lower margin: Varies from Greyed-Yellow (162C) to Yellow (10B). Lower center: Greyed-Green (191B).

Texture: Glabrous.

Apex: Obtuse.

Base: Cuneate.

Margin: Entire.

Texture: Glabrous all surfaces.

Venation: Pinnate.

Vein color:

*Upper.*—Varies with the color of the variegation and ranges between and includes Yellow (10A), Greyed-Yellow (162C) or Greyed-Green (191A).

*Lower.*—Varies with the color of the variegation and ranges between and includes Yellow (10B), Greyed-Yellow (162D) or Greyed-Green (191B).

Leaf attachment: Petiolate.

Petiole:

*Length.*—Avg. 0.3 cm (0.1 to 0.5 cm).

*Width.*—About 0.1 cm.

*Color.*—Green (NN137A) with margin of Yellow (10C).

*Texture.*—Glabrous.

INFLORESCENCE

None observed.

REPRODUCTIVE ORGANS

None observed.

OTHER CHARACTERISTICS

Fruit and seed: None observed.

Disease and insect resistance: No significant disease or insect pests have been observed.

Cold hardiness: Hardy to USDA zone 6b; testing has not been completed in colder zones.

CITATIONS

Edwards, D, J. H. C. Griffin, and J. D. Armitage. 2015. A molecular and morphological investigation into the origins of *Ligustrum* x *vicaryi* (Oleaceae) with consideration of its nomenclature. New J. Botany. 5(2):101-118.

What is claimed is:

1. A new and distinct variety of *Ligustrum* plant named 'NCLO1' as illustrated and described herein.

* * * * *